(12) United States Patent
Srinivas et al.

(10) Patent No.: US 6,723,856 B1
(45) Date of Patent: Apr. 20, 2004

(54) PROCESS FOR THE PREPARATION OF 2-ACETYL-1-PYRROLINE, THE BASMATI RICE FLAVORANT

(75) Inventors: Pullabhatia Srinivas, Karnataka (IN); Kambadoor Nagarajarao Gurudutt, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/400,913

(22) Filed: Mar. 28, 2003

(51) Int. Cl.[7] .............................................. C07D 207/00

(52) U.S. Cl. ...................................................... 548/540

(58) Field of Search ......................................... 548/540

(56) References Cited

U.S. PATENT DOCUMENTS 4,522,838 A * 6/1985 Buttery et al. ............... 426/537
5,446,171 A * 8/1995 Duby et al. .................. 548/540

OTHER PUBLICATIONS

Hofman et al., Journal of Agricultural and Food Chemistry, 46(2), 616–619, 1998.*

* cited by examiner

*Primary Examiner*—Fiona T. Powers
(74) *Attorney, Agent, or Firm*—Arent Fox, PLLC; Wilburn L. Chesser

(57) ABSTRACT

The present invention provides a process for preparing of 2-acetyl-1-pyrroline, the principle aroma component of basmati and other varieties of scented rice, and also of processed cereal and grain products, said flavor chemical is of great value, in the art of application of flavor to foodstuffs like rice and bakery products.

9 Claims, No Drawings

PROCESS FOR THE PREPARATION OF 2-ACETYL-1-PYRROLINE, THE BASMATI RICE FLAVORANT

FIELD OF THE INVENTION

The present invention relates to 'an improved process for the preparation of 2-acetyl-1-pyrroline, the principle aroma component of basmati and other varieties of scented rice and also of processed cereal and grain products'.

The main uses of the present invention are, i) preparation of 2-acetyl-1-pyrroline by a simple process and ii) making the aroma chemical in grams. The flavor chemical is of great value, in the art of application of flavor to foodstuffs like rice and bakery products.

BACKGROUND AND PRIOR ART REFERENCES

Scented varieties of rice[1-6] will have a characteristic, strong aroma when cooked. 'Basmati' varieties in Southeastern Asia, 'Della' in America, 'Milagrosa' in Philippines, 'Khao Dawk Mali 105' in Thailand, 'Seratus Malam' in Indonesia and 'Heiri' in Japan are examples of such varieties. All over the world, they are highly valued and used in making rice dishes and other food products.

2-acetyl-1-pyrroline was first identified in 1982 by Buttery et al[7-8], who described its odour as that of cooked rice and popcorn-like. They also described a method of its synthesis from 2-acetylpyrrole[9]. Also, a method for its quantitative analysis was developed by Buttery et al[10] and refined later by Tanchotikul et al[11]. It can be used, among other things, to evaluate the flavor of new rice varieties. Steam distillation cum continuous extraction isolation procedure (Likens-Nickerson method) is used for isolating the rice flavor. 2,4,6-trimethylpyridine (collidine) is added as internal standard to the flask containing rice and water. The volatile basic fraction is separated from other volatiles that are extracted into the organic solvent (diethyl ether) by adding dilute sulfuric acid and stirring. In this way, compounds interfering in the GC analysis are removed. After extraction, the basic compounds are regenerated from the aqueous acid by neutralization with excess sodium bicarbonate and re-extracted with ether. The extract after concentration (~to 0.05 ml), can be analyzed by GC. The amount of 2-Acetyl Pyrroline (AP) is calculated by the following equation.

$$\text{2-AP concentration (ppb)} = \frac{\text{area of AP peak}}{\text{area of TMP peak}} \times 150 \times 3.57 \times 5$$

A recovery factor of 28% is recommended, for inclusion as determined by the stability of pure 2-AP, under the conditions employed for extraction. Hence, it is necessary to multiply the results based on the internal standard and then by the factor 100/28=3.57 to get the amount of 2-acetyl-1-pyrroline actually present in the cooked rice. The factor 150 is the number of micrograms of the internal standard added and the factor 5 is needed to convert to ppb. Another method by Tonchitkul et al[11]., employs the SDE method for extraction and selected ion monitoring (SIM) in GC-MS for detection and quantification of 2-acetyl-1-pyrroline and trimethylpyridine. 2-AP is found to be present in all scented rice varieties in quantities ranging from 300 to 750 ppb.

Mol. formula: $C_6H_9ON$;
Mol. Wt. 111;
CAS Registry No:85213-22-5;
Structural Formula

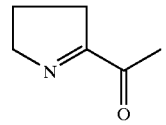

2-acetyl-1-pyrroline can be characterized by a comparison of its retention time and MS data with those of a reference standard or those reported in literature. The mass spectrum of 2-acetyl-1-pyrroline has major peaks at m/z 111($M^+$, 5% abundance, 83 (11), 69 (11), 68 (8), 55(2), 52 (0.2) and 43 (100), 42 (24) and 41 (50). It's Kovats index is 1320 on a Pyrex glass capillary column coated with Carbowax 20M. Its IR spectrum in $CCl_4$ displays absorption maxima at 1695, 1620, 1435, 1370, 1340, 1250, 1080, 1000, 975 and 940 $cm^{-1}$.

The compound is a colorless liquid when freshly prepared and purified. It must be protected from light and air and preserved in sealed vials under vacuum at temperatures below −20° C. Even under these conditions, it is reported to turn to red and eventually become very dark on long storage. A conjugated polymer, resulting from the coupling of the carbonyl group of one molecule with the 5-position of another molecule, is believed to be the product formed in the process[9]. For this reason the compound is more stable and better preserved in dilute solutions, especially aqueous ones, for several months at less than 20° C.

It seems reasonable to assume that 2-acetyl-1-pyrroline has a similar origin to the bread aroma compound, 2-acetyl-1,4,5,6-tetrahydropyridine[12]. It is assumed that the intermediate formed after decarboxylation of proline residue, is hydrolyzed with the formation of 1-pyrroline. 2-acetyl-1-pyrroline results from the acetylation 1-pyrroline by 2-oxopropanal. Many syntheses of 2-acetyl-1-pyrroline are reported in recent literature[13-17].

Reference may be made to the synthetic method (Buttery et al. *J. Agric. Food Chem.* 1983, 31, 823–826) starting from 2-acetyl-1-pyrrole. The main drawback of this procedure is that it employs, for reduction, expensive rhodium on alumina catalyst in stoichiometric quantities, because its activity is lost during the reaction. The subsequent oxidative step is inefficient as it affords low yields (less than 10%) and the product requires sophisticated preparative GC for purification.

Reference may be made to the synthetic method of DeKimpe N G et al. (*J. Agric. Food Chem.* 1993, 41, 1458–1461), wherein pyrrolidine is converted into tripyrroline, which on hydrocyanation yields 2-cyano-1-pyrroline in two steps and subsequently to 2-acetyl-1-pyrroline by Grignard reaction with methylmagnesium bromide or iodide. The main drawback of this procedure is that it has multiple steps and employs potassium cyanide reagent and generation of hydrogen cyanide, both of which are highly toxic.

Reference may be made to another method (Guttmann S, Helv. Chim Acta 1961, 44, 721–744; Hausler and Schmidt, Liebigs Ann. Chem. 1979, 1881–1889; Poisel H and Schmidt U, Chem Ber, 1975, 108, 2547–2553) wherein proline is converted to its methyl ester by passing dry HCl through a methanolic solution of proline or by reaction with thionyl chloride in dry methanol. The drawback of both these methods is that they involve laborious steps of repeated methanol addition and its removal to obtain the hydrochloride of the methyl ester. The methyl ester is then liberated and dried for N-chlorination followed by dehydrohalogenation using triethylamine to afford 2-(methoxycarbonyl)-1-pyrroline. This reaction is very slow (>24 h) and it also gives rise to side products. This precursor is then treated with methylmagnesium iodide to afford 2-acetyl-1-pyrroline.

Reference may be made to another method (Hoffmann T and Schieberle P, *J. Agric. Food Chem.* 1998, 46, 616–619) wherein 2-acetyl-1-pyrroline is prepared from N-(tert-butoxycarbonyl)-1-proline in four steps. The drawback of this invention is that it involves sulfur containing 2-pyridylthio intermediate, traces of which could interfere with the olfactory purity of the flavourant.

Reference may be made to yet another study (Favino T F et al. J. Org. Chem. 1996, 61, 8975–8979) wherein 2-acetyl-1-pyrroline is prepared by Penicilin acylase-mediated hydrolysis of 1-[(N-phenylacetyl)amino]4,5-dioxohexane to 1-amino4,5-diketone compound followed by spontaneous ring closure of the latter. The drawback of this method is that, the preparation of N-phenylacetamide derivative involves multiple steps of conversion starting from cis-3-hexenol via the corresponding acetylenic C-6 amine.

OBJECTS OF THE INVENTION

The main objective of the present invention is to develop 'an improved process for preparation of 2-acetyl-1-pyrroline, a principal basmati aroma component', which obviates the aforesaid drawbacks of the processes described in the prior art.

SUMMARY OF THE INVENTION

Accordingly, the present invention provides, an improved process for preparation of 2-acetyl-1-pyrroline, the basmati rice flavourant', by synthesis of 2-acetyl-1-pyrroline by an improved and novel method from proline.

DETAILED DESCRIPTION OF THE INVENTION

In accordance to the objectives, the present invention provides a process for the preparation of 2-acetyl-1-proline, the said process comprising steps of:

a) dissolving L-pyrroline in dry alcohol, cooling to a temperature in the range of −5° C. to −15° C., b) adding thionylchloride to step (a) solution, maintaining the temperature of reactant mixture below 0° C., c) stirring the reactant mixture of step (b) at a temperature range of 20° to 30° C. for a time period of 1 h to 4 h, d) removing the solvent from reactant mixture of step (c) to obtain a residue, which is stored in ice-chest for a time period of 10 hours to 16 hours to obtain a solid mass, e) adding the solid mass of step (d) to 50% aqueous alkali carbonate solution, extracting with an organic solvent, separating the organic and aqueous layer, f) drying the organic layer of step (e) over anhydrous sodium sulphate, filtering, evaporating the solvent from filtrate to obtain a residue, g) distilling the residue of step (f) to obtain 2-carbomethoxy-1-pyrrolidine, h) dissolving 2-carbomethoxy-1-pyrrolidine of step (g) in ether, cooling to a temperature range of 0° to 5° C., adding drop wise t-butylhypochlorite over a period of 10 minutes to 30 minutes, stirring at a temperature range of 20° to 30° C. for a time period of 4 h to 6 h, i) filtering the solution of step (h), removing the solvent from the filtrate to obtain 2-carbomethoxy-1-pyrroline, j) preparing Grignard Reagent in dry ether by adding magnesium turning, iodine followed by dropwise methyl iodide and stirring at a temperature in the range of 25° C. to 35° C. for completion of reaction, cooling the mixture to 0° C., k) adding an ethereal solution of 2-carbomethyoxy-1-pyrroline to the cooled mixture of step (j), stirring at a room temperature till the reaction is complete, i) adding 5% aqueous hydrochloric acid to step (k) mixture, extracting with diethyl ether, separating the organic layer, drying the organic layer over anhydrous sodium sulphate, filtering to obtain a filtrate, and j) distilling the filtrate of step (i) to obtain pure 2-acetyl-1-pyrroline.

In an embodiment of the invention relates to use of dry alcohol, which is selected from a group consisting of dry methanol, ethanol and propanol, preferably methanol.

Another embodiment, the organic solvent used is selected from a group consisting of dimethyl ether, diethyl ether and di-isopropyl ether, preferably diethyl ether.

Another embodiment, the aqueous alkali carbonate solution used, is selected from a group consisting of 50% aqueous sodium carbonate or 50% aqueous potassium carbonate.

Still another embodiment, the dehydrogenation can be performed using potassium acetate.

Still another embodiment, the 2-acetyl-1-pyrroline obtained has a basmati rice flavor or popcorn flavor.

Still another embodiment, the 2-acetyl-1-pyrroline obtained is used in flavoring agent in food products, bakery products, food drinks and rice products.

In an embodiment of the present invention, proline was converted to 2-(carbomethoxy)pyrrolidine by reaction with thionyl chloride under mild conditions.

In yet another embodiment of the invention, 2-(carbomethoxy)-N-chloropyrrolidine was dehydrohalogenated by reaction with potassium t-butoxide or potassium acetate at ambient temperatures.

In another embodiment of the present invention, 2-(carbomethoxy)-1-pyrroline was converted to 2-acetyl-1-pyrroline by a known Grignard reaction with methylmagnesium iodide.

The following examples are given by way of illustration of the present invention and therefore should not be construed to limit the scope of the present invention.

EXAMPLE 1

A solution of L-proline (2.23 g) in dry methanol (15 ml) was cooled to −5° C. and thionyl chloride (4.52 g) was added dropwise, while stirring and maintaining the temperature of the reactants below 0° C. The reaction was continued at 25° C. for 2 h. The solvent was distilled and the residue stored in ice-chest for 12 h. The solid mass was added to aqueous solution of potassium carbonate (50%, 20 ml) at 0° C. and the separated oily layer was extracted into ether (15 ml×3). The ethereal layer was dried over anhydrous sodium sulfate and distilled to afford 2.3 g of 2-(carbomethoxy)-pyrrolidine (85%), [MS (m/z) M$^+$129 (1%), 114 (0.5), 70(100), 68(50), 43(80), 41(90)]. It was taken in dry diethyl ether (15 ml), cooled to 0° C. and t-butylhypochlorite (2.16 g) added dropwise. The reaction was monitored on silica gel thin layer using chloroform as the eluant. After completion of the reaction (15 min.), potassium t-butoxide (2.24 g) was added gradually over 10 min. and the reactants stirred at 25° C. for 5 h. The solution was filtered and the solvent distilled under reduced pressure to afford 2-(carbomethoxy)-1-pyrrroline (2 g), [MS (m/z) M$^+$ 127(1%), 112(0.5), 97 (15), 69 (100), 54 (50), 41 (75)]. To a suspension of magnesium turnings (0.43 g) in dry ether, iodine (0.01 g) was added followed by dropwise addition of a solution of methyl iodide (3.08 g) in ether (5 ml) at 35° C. The mixture was stirred until the disappearance of magnesium turnings (15 min), then cooled to 0° C. To it, a solution of 2-(carbomethoxy)-1-pyrrroline (2 g) in dry ether (5 ml) was added over 5 min. and the mixture was stirred at room temperature. On completion of the reaction (2 h) the product was worked up by the addition of dilute hydrochloric acid (5%, 10 ml) and the organic layer separated. The aqueous layer was further extracted with ether (10 ml×2) and the combined organic layers dried over anhydrous sodium sulphate and distilled to afford pure 2-acetyl-1-pyrroline [1.3g, 95% purity, MS (m/z) M$^+$ 111 (5%), 96 (0.1), 83 (15), 69(8), 68 (10), 55 (2), 52 (0.2), 43 (100),42 (25), 41 (50)].

EXAMPLE 2

To a solution of L-proline (2.23 g) in dry methanol (15 ml) cooled to −5° C., thionyl chloride (4.52 g) was added drop wise, while stirring and maintaining the temperature of the reactants below 0° C. The reaction mixture was allowed to attain room temperature (25° C.) and further stirred for 2 h. The solvent was distilled off from it and the residue stored in ice-chest for 12 h. The solid mass that separated was added to an aqueous potassium carbonate solution (50%, 20 ml) at 0° C. and the separated oily layer extracted into ether (15 ml×3). The combined ethereal layers were dried over anhydrous sodium sulfate and distilled to afford 2.3 g of 2-(carbomethoxy)-pyrrolidine [85%, MS (m/z) M$^+$129 (1%), 114 (0.5), 70(100), 68(50), 43(80), 41(90)]. To an ice-cooled solution of the compound in dry diethyl ether (15 ml), t-butylhypochlorite (2.16 g) was added drop-wise. The reaction was monitored on thin layer of silica gel using chloroform as the eluant. After 15 min. anhydrous potassium acetate (2.76 g) was added gradually to it over 10 min., and the mixture stirred at 25° C., while monitoring the reaction by TLC. At the end of the reaction (3 h), the solution was filtered and the solvent distilled under reduced pressure to afford 2-carbomethoxy)-1-pyrrroline [Yield: 1.9 g, MS (m/z) M$^+$ 127(1%), 112(0.5), 97 (15), 69,(100), 54 (50), 41 (75)]. To a suspension of magnesium turnings (0.43 g) in dry diethylether, iodine (0.01 g) was added followed by a solution of methyl iodide (3.08 g) in ether (5 ml) dropwise at 35° C. The mixture was stirred until the disappearance of magnesium (15 min) and then after cooling to 0° C., a solution of 2-(carbomethoxy)-1-pyrrroline (1.9 g) in dry diethylether (5 ml) was added over 5 min. On completion of the reaction (2 h) as found by GC, the product was worked up by addition of dilute hydrochloric acid (5%, 10 ml) and separation of the organic layer. The aqueous layer was further extracted with diethylether (10 ml×2) and the combined organic layers dried over anhydrous sodium sulphate. Removal of the solvent afforded pure 2-acetyl-1-pyrroline [1.2 g, 95% purity, MS (m/z) M$^+$ 111 (5%), 96 (0.1), 83 (15), 69(8), 68 (10), 55(2), 52 (0.2), 43 (100), 42 (25), 41 (50)].

REFERENCES

1. *Volatile Compounds in Foods and beverages*, Maarse H, Marcel Dekker, New York, 1991, pp79–89.
2. Buttery R G, Tumbaugh J G and Ling L C, Contribution of volatile to rice aroma, *J Agric Food Chem.*, 1988, 36(5), 1006–1009
3. Lin C F, Hsieh, T C.-Y and Hoff B J, Identification and quantification of the "popcorn'-like aroma in Louisiana and della rice (Oryza sativa, L.), *J Food Sci*, 1990, 55(5), 1466–1469
4. Seitz L M, Wright R L, Waniska R D and Rooney L W, Contribution of 2-acetyl pyrroline to odors from wetted ground pearl millet, *J Agric Food Chem*, 1993,41(6), 955–958.
5. Widjaja R, Craske J D and Wootton M, Comparative studies on volatile components of non-fragrant and fragrant rices, *J Sci Food Agric*, 1996, 70,151–161.
6. Paule C M and Powers J J, Sensory and chemical examination of aromatic and on-aromatic rices, *J Food Sci.*, 1989, 54(2), 343–346.
7. Buttery R G Ling L C and Juliano B O, 2-acetyl-1-pyrroline: an important aroma component of cooked rice, *Chem and Ind*, 1982, 958–959
8. Buttery R G, Juliano B O and Ling L C, Identification of rice aroma compound 2-acetyl-1-pyrroline in pandana leaves, *Chem and Ind*, 1983, 478
9. Buttery R G, Ling L C, Juliano B G and Tumbaugh J G, Cooked rice aroma and 2-acetyl pyrroline, *J Agric Food Chem*, 1983, 31(4), 823–826.
10. Buttery R G, Ling L C and Mon T R, Quantitative analysis of 2-acetyl pyrroline, *J Agric Food Chem*, 1986, 34(1), 112–114
11. Tanchotikul U and Hsieh T C.-Y, An improved method for quantification of 2-acetyl-1-pyrroline, a "popcorn"-like aroma, in aromatic rice by high-resolution gas chromatography/mass spectrometry/selected ion monitoring, *J Agric Food Chem*, 1991, 39 (5), 944–947.
12. Schieberle P and Grosch W, Identification of the volatile flavour compounds of wheat bread crust—comparison with rye bread crust, Zeitschrift *fur Lebensmittel unterschung and Forchung*, 1985, 180(6), 474–478.
13. De Kimpe N, Stevens C V and Keppens M, Synthesis of 2-acetyl pyrroline, the principle rice flavour component, *J Agric Food Chem*, 1993, 41(9), 1458–1461.
14. De Kimpe N and Keppens M, Novel syntheses of the major flavour components of bread and cooked rice, *J Agric Food Chem*, 1996,44(6), 1515–1519
15. Hofman T and Schieberle P, New and convergent synthesis of the important roasty, pop-corn smelling food aroma compounds, 2-acetyl-1-pyrroline and 2-acetyltetrahydropyridine from their corresponding cyclic α-amino acids, *J Agric Food Chem*, 1998, 46(6), 2270–2277
16. Hofman T and Schieberle P, Pencilin acylase-mediated synthesis of 2-acetyl-1-pyrroline and 2-propionyl-1-pyrroline, key roast smelling odourant in Food. Inclusion complexes with β-cyclodextrin and their NMR & MS characterization, *J Agric Food Chem.*, 1998, 46(6), 616–619.
17. Favino T F, Fronza G, Fuganti C, Fuganti D, Grasselli and Mele A, 2-oxopropanol, hydroxy-2-propanone and 1-pyrroline—important intermediates in the generation of the roast smelling food flavour compounds, 2-acetyl-1-pyrroline and 2-acetyltetrahydropyridine, *J Org chem.*, 1996, 61(25), 8975–8979.

What is claimed is:
1. An improved process for the preparation of 2-acetyl-1-pyrroline, the said process comprising steps of:
   a) dissolving L-proline in dry alcohol, cooling to a temperature in the range of −5° C. to −15° C.,
   b) adding thionylchloride to step (a) solution, maintaining the temperature of reactant mixture below 0° C.,
   c) stirring the reactant mixture of step (b) at a temperature range of 20° to 30° C. for a time period of 1 h to 4 h, d) removing the solvent from reactant mixture of step (c) to obtain a residue, which is stored in ice-chest for a time period of 10 h to 16 h to obtain a solid mass, e) adding the solid mass of step (d) to 50% aqueous alkali carbonate solution, extracting with an organic solvent, separating the organic and aqueous layer, f) drying the organic layer of step (e) over anhydrous sodium sulphate, filtering, evaporating the solvent from filtrate to obtain a residue, g) distilling the residue of step (f) to obtain 2-carbomethoxy-1-pyrrolidine, h) dissolving 2-carbomethoxy-1-pyrrolidine of step (g) in ether, cooling to a temperature range of 0° to 5° C., adding drop wise t-butylhypochlorite over a period of 10 minutes to 30 minutes, stirring at a temperature range of 20° to 30° C. for a time period of 4 h to 6 h, i) filtering the solution of step (h), removing the solvent from the filtrate to obtain 2-carbomethoxy-1-pyrroline, j) preparing Grignard Reagent in dry ether by adding magnesium turning, iodine followed by dropwise methyl iodide and stirring at a temperature in the range of 25° C. to 35° C. for completion of reaction, cooling the mixture to 0° C., k) adding an ethereal solution of 2-carbomethyoxy-1-pyrroline to the cooled mixture of step (j), stirring at a room temperature till the reaction is complete, k) adding 5% aqueous hydrochloric acid to step (k) mixture, extracting with diethyl ether, separating the organic layer, drying the organic layer over anhydrous sodium sulphate, filtering to obtain a filtrate, and l) distilling the filtrate of step (i) to obtain pure 2-acetyl-1-pyrroline.

2. The process of claim 1, wherein in step (a) the dry alcohol used, is selected from a group consisting of dry methanol, ethanol and propanol.

3. The process of claim 2, wherein the dry alcohol used is dry methanol.

4. The process of claim 1, wherein in step (e) the organic solvent used is selected from a group consisting of dimethyl ether, diethyl ether and di-isopropyl ether.

5. The process of claim 4, wherein the solvent used is diethyl ether.

6. The process of claim 1, wherein in step (e) the aqueous alkali carbonate solution used, is selected from a group consisting of 50% aqueous sodium carbonate and 50% aqueous potassium carbonate.

7. The process of claim 1, wherein in step (h) the dehydrogenation can be performed using potassium acetate.

8. The process of claim 1, wherein the 2-acetyl-1-pyrroline obtained has a basmati rice flavor or popcorn flavor.

9. The process of claim 1, wherein the 2-acetyl-1-pyrroline obtained is used in flavoring agent in food products, bakery products, food drinks and rice products.

* * * * *

UNITED STATES PATENT AND TRADEMARK OFFICE
CERTIFICATE OF CORRECTION

PATENT NO. : 6,723,856 B1
DATED : April 20, 2004
INVENTOR(S) : Srinivas et al.

It is certified that error appears in the above-identified patent and that said Letters Patent is hereby corrected as shown below:

<u>Title page,</u>
Item [57], Inventors, should read as follows:
-- Srinivas Pullabhatla, Karnataka (IN) --.

Signed and Sealed this

Fourteenth Day of December, 2004

JON W. DUDAS
*Director of the United States Patent and Trademark Office*